United States Patent
Bhandari et al.

(10) Patent No.: US 8,709,354 B2
(45) Date of Patent: Apr. 29, 2014

(54) METHODS OF MAKING A DIAGNOSTIC DEVICE BY INTERWEAVING HYDROPHOBIC AND HYDROPHILIC FIBERS, AND DIAGNOSTIC DEVICE THEREFROM

(75) Inventors: Paridhi Bhandari, Bangalore (IN); Dhananjaya Dendukuri, Bangalore (IN); Vijayakumar Ganapathy, Kanchipuram (IN); Srinivasan Kandaswamy, Little Kanchipuram (IN); Diya Lewis, Chennai (IN)

(73) Assignee: Achira Labs Pvt. Ltd., Bangalore (IN)

( * ) Notice: Subject to any disclaimer, the term of this patent is extended or adjusted under 35 U.S.C. 154(b) by 0 days.

(21) Appl. No.: 13/702,947

(22) PCT Filed: Sep. 3, 2010

(86) PCT No.: PCT/IB2010/053976
§ 371 (c)(1),
(2), (4) Date: Dec. 7, 2012

(87) PCT Pub. No.: WO2012/004636
PCT Pub. Date: Jan. 12, 2012

(65) Prior Publication Data
US 2013/0095506 A1    Apr. 18, 2013

(30) Foreign Application Priority Data
Jul. 5, 2010  (IN) .......................... 1908/CHE/2010

(51) Int. Cl.
*B01L 3/00*    (2006.01)

(52) U.S. Cl.
USPC ................ 422/502; 435/7.1; 435/4

(58) Field of Classification Search
None
See application file for complete search history.

(56) References Cited

U.S. PATENT DOCUMENTS

| | | | | |
|---|---|---|---|---|
| 4,046,514 A | * | 9/1977 | Johnston et al. | 422/420 |
| 5,217,447 A | * | 6/1993 | Gagnon | 604/397 |
| 2009/0004737 A1 | * | 1/2009 | Borenstein et al. | 435/395 |

FOREIGN PATENT DOCUMENTS

WO   WO 2009121043 A2 *  10/2009 ............. G01N 35/00

OTHER PUBLICATIONS

Nam et al., Morphology of Regenerated Silk Fibroin: Effects of Freezing Temperature, Alcohol Addition, and Molecular Weight, Journal of Applied Polymer Science 81:2008-3021, 2001.*
Interweave. (2000). In Collins English Dictionary. Retrieved from http://www.credoreference.com/entry/hcengdict/interweave.*

* cited by examiner

*Primary Examiner* — Mark Shibuya
*Assistant Examiner* — Andrea S Grossman
(74) *Attorney, Agent, or Firm* — Levine Bagade Han LLP

(57) ABSTRACT

In one aspect, the invention provides a method for making a hydrophilic-silk composition. The method includes providing at least one strand of silk fiber, treating the silk fiber with an alkaline solution to provide at least one strand of degummed silk fiber, and treating the degummed silk fiber with a treatment solution to provide a hydrophilic-silk composition. The degummed silk fiber or the hydrophilic-silk composition is further immobilized with at least one reagent to make a silk-based diagnostic composition. The invention provides a silk-based diagnostic composition made by the method of the invention, and a diagnostic device that comprises the silk-based diagnostic composition. In another aspect, the invention provides a method of making a diagnostic device. The method includes providing at least one strand of a diagnostic-fiber composition, providing at least one strand of a hydrophobic-fiber composition, inter-weaving the at least one strand of the diagnostic-fiber composition and the at least one strand of the hydrophobic-fiber composition. In one embodiment, the diagnostic-fiber composition and the hydrophobic-fiber composition are both based on silk.

14 Claims, 11 Drawing Sheets

20

22 — Providing at least one strand of diagnostic-fiber composition

24 — Providing at least one strand of hydrophobic-fiber composition

26 — Inter-weaving

Fig. 1

METHODS OF MAKING A DIAGNOSTIC DEVICE BY INTERWEAVING HYDROPHOBIC AND HYDROPHILIC FIBERS, AND DIAGNOSTIC DEVICE THEREFROM

CROSS-REFERENCE TO RELATED APPLICATIONS

This application is a U.S. National Phase under 35 U.S.C. 371 to PCT International Patent Application No. PCT/IB2010/053976 filed on Jul. 5, 2010, the content of which is incorporated herein by reference in its entirety.

TECHNICAL FIELD

The invention relates generally to methods of making diagnostic devices that involve interweaving of hydrophobic and hydrophilic fibers, and to diagnostic devices resulting therefrom.

BACKGROUND

The detection of analytes including proteins, DNA/RNA and metabolites from body fluids and other samples of biological origin is essential for a variety of applications including medical testing, toxin detection and forensic analysis. Improved, point-of-care testing of such analytes is an urgent worldwide requirement (Yager, P.; Domingo, G. J.; Gerdes, J., Point-of-care diagnostics for global health. *Annu Rev Biomed Eng* 2008, 10, 107-44). The current systems designed for such applications suffer from several drawbacks such as high costs, bulkiness and delayed results. There is therefore a large unmet need for the development of systems that are low-cost, portable, convenient to handle and show high efficiency towards detection. These systems should also be capable of rapidly identifying a broad range of analytes from samples of biological origin.

Microfluidic, lab-on-a-chip methods have gained prominence over the past decade as solutions to some of these problems. However, existing technologies for the manufacture of microfluidic lab-on-a-chip devices are handicapped by the absence of mature manufacturing processes that can enable the transition of ideas from academic labs to industry. Adaptation of traditional methods used for microelectronic fabrication for this purpose meant that early microfluidic devices were synthesized in glass or silicon. However, these are materials that require expensive processing conditions and high capital investment.

To address this problem, a number of different materials and processing methods have been explored for the fabrication of microfluidic devices (Becker, H.; Locascio, L. E., Polymer microfluidic devices. *Talanta* 2002, 56 (2), 267-287). These materials include plastics such as PDMS (polydimethylsiloxane) (McDonald, J. C.; Whitesides, G. M., Poly (dimethylsiloxane) as a material for fabricating microfluidic devices. *Acc Chem Res* 2002, 35 (7), 491-9), PMMA (polymethylmethacrylate) (Klank, H.; Kutter, J. P.; Geschke, O., CO(2)-laser micromachining and back-end processing for rapid production of PMMA-based microfluidic systems. *Lab Chip* 2002, 2 (4), 242-6) and COC (cyclicolefin copolymer) (Pu, Q.; Oyesanya, O.; Thompson, B.; Liu, S.; Alvarez, J. C., On-chip micropatterning of plastic (cylic olefin copolymer, COC) microfluidic channels for the fabrication of biomolecule microarrays using photografting methods. *Langmuir* 2007, 23 (3), 1577-83). Plastics are relatively cheap and they have advantages such as their processability, transparency and the ability to form intricate patterns down to the micron scale. However, they also suffer from some disadvantages such as their natural hydrophobic nature which precludes simple capillary flow, their carbon footprint and the lack of mature manufacturing methods that are easily adaptable for large scale microfluidic plastic chip fabrication. Further, for the plastic-based microfluidic devices, sophisticated and expensive readers that can direct fluid flow and can provide a read-out from the plastic chip are still required, which renders the entire device and operation unsuitable for very low-cost and robust point-of-care diagnostics.

On the other hand, paper-based lateral flow immunoassays (LFIs) have been hugely successful in the market place with a variety of rapid tests such as home pregnancy tests being widely available. Visual readouts in the form of a color change are used for detection while sample flow occurs automatically through capillary action. Further, mature manufacturing processes are already available for such devices. However, LFIs come with a set of disadvantages too. They are not very reliable and do not provide for the ability to perform multiplex tests. One of the reasons for this is the lack of an ability to define a 'flow-path' in a paper based device (Martinez, A. W.; Phillips, S. T.; Butte, M. J.; Whitesides. G. M. Patterned paper as a platform for inexpensive, low-volume, portable bioassays. *Angew Chem Int Ed Engl* 2007, 46 (8), 1318-20).

Recently, the Whitesides group advanced such technology by patterning paper into selectively hydrophilic and hydrophobic portions. A patterned flow field can therefore be defined. However, paper-based devices still have some problems like the lack of mechanical stability and the absence of low-cost manufacturing methods that can deposit multiple reagents without heat treatment or exposure to high stress. Very recently, cotton thread has also been explored as a medium for microfluidic chip fabrication (Li, X.; Tian, J. Shen, W., Thread as a Versatile Material for Low-Cost Microfluidic Diagnostics. *ACS Applied Materials & Interfaces* 2009, 2 (1), 1-6). Experiments were performed on single cotton threads or cotton threads that have been sewed onto a plastic substrate and color change based readouts were used to detect the presence of a reagent. These experiments are not necessarily conducive towards development of high-throughput and reproducible methods for manufacture of point-of-care diagnostic devices using either the cotton fibers or other suitable materials. Hence, there remains a dire need in the art that addresses all the problems associated with diagnostic devices, their manufacture, cost and reliability.

BRIEF DESCRIPTION

In one aspect, the invention provides a method of making a diagnostic device. The method comprises providing at least one strand of a diagnostic-fiber composition. The method then comprises providing at least one strand of a hydrophobic-fiber composition. The method then involves inter-weaving the at least one strand of the diagnostic-fiber composition and the at least one strand of the hydrophobic-fiber composition.

In yet another aspect, the invention provides a diagnostic device. The diagnostic device comprises at least one strand of a diagnostic-fiber composition and at least one strand of a hydrophobic-fiber composition that are inter-woven.

DRAWINGS

These and other features, aspects, and advantages of the present invention will become better understood when the following detailed description is read with reference to the accompanying drawings in which like characters represent like parts throughout the drawings, wherein:

FIG. 1 is a flowchart representation of the exemplary steps of the method for making a diagnostic device of the invention;

DETAILED DESCRIPTION

Figure 2:
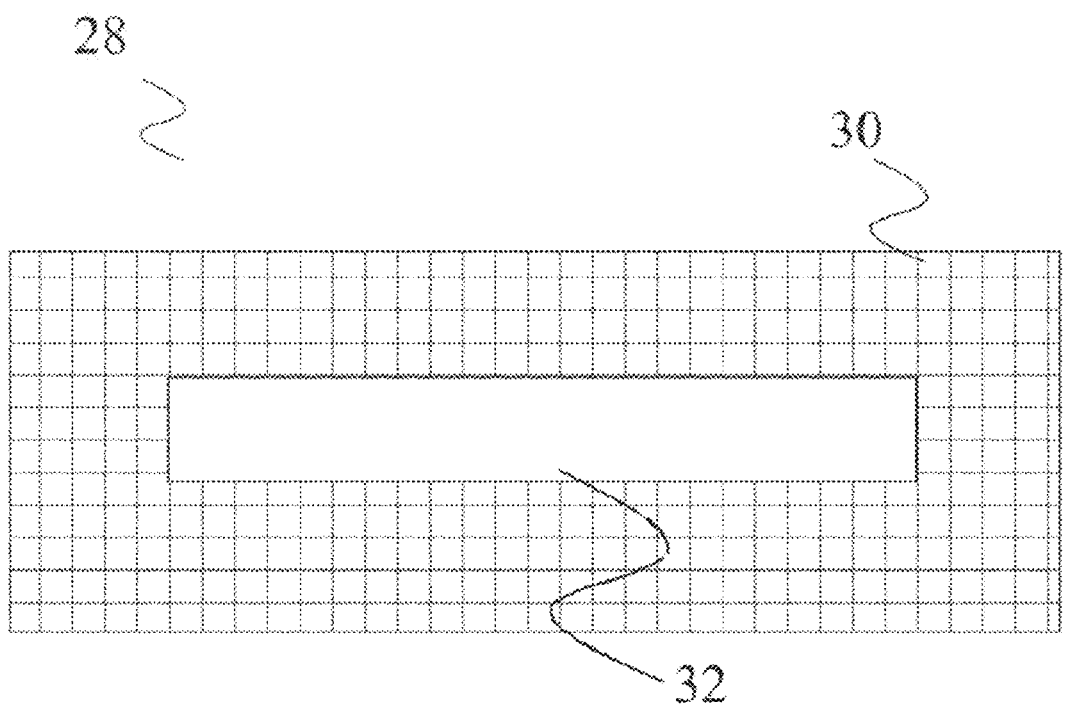
FIG. 2 is a schematic representation of an exemplary diagnostic device of the invention.

As used herein and in the claims, the singular forms "a," "an," and "the" include the plural reference unless the context clearly indicates otherwise.

Strand as used herein refers to a single element (as a yarn or thread) of a woven or plaited material.

Analyte, as used herein, refers to a substance or chemical constituent that is determined in an analytical procedure. For instance, in an immunoassay, the analyte may be a protein ligand or a binder, while in blood glucose testing, the analyte is glucose. In one instance, the analyte could be a gene that is a marker for the Hepatitis-B virus. In another exemplary instance, analyte may include a drug to be detected, such as cocaine from a blood analysis. The analytical procedure may include, for instance, fluorescence, mass-spectrometry, colorimetry, radio-imaging, electrochemical detection and the like, and combinations thereof. In some instances, analytes may refer to antibodies. In other instances, analytes may refer to antigens.

Antibody as used herein refers to protein that is used in the identification of specific antigen. The specific antigen is typically a marker of a disease or certain types of diseases. Sometimes, antibodies may also be referred to as immunoglobulins. Antibody may be primary or secondary antibody. Primary antibodies are antibodies raised against a specific antigen and are generally unlabelled. Primary antibodies may also be referred to as capture antibodies. Secondary antibody is an antibody that binds to primary antibody or fragments contained within the primary or capture antibody. Secondary antibody comprise label that render them useful for detection. Typical labels include fluorescence moiety, radio-active compounds, enzyme-linked labels, magnetically active particles, nanoparticles, quantum dots, latex particle labels, and the like, and combinations thereof. Depending on the label, the method used to detect, identify and quantitate may include fluorescence spectroscopy, radio-imaging, ELISA test and the like.

Antigen, as used herein, refers to a molecule that is recognized by an immune system of a living organism. Antigen also refers to molecular fragments that may be recognized by the immune system. It is generally known that a given antigen shows specificity to an antibody, and this property of an antigen is used in a variety of applications.

As stated herein, in one aspect, the invention provides a method of making a diagnostic device, represented by numeral 20 in FIG. 1. The method includes providing at least one strand of a diagnostic-fiber composition, shown in FIG. 2 and represented by numeral 22. The diagnostic fiber composition comprises a fiber made from a hydrophilic polymer. As used herein, hydrophilic polymer is a polymer that is capable of being wet with water. Hydrophilicity of a polymer is generally understood by the physical phenomena of wicking, as measured by wicking rate. Hydrophilicity may also be understood by the contact angle made by the water droplet on the surface of the polymer. The hydrophilic polymers useful in the invention must also have the ability to form fibers. Useful hydrophilic polymers for the diagnostic-fiber composition include, but not limited to, poly(vinyl alcohol), degummed silk, cotton, rayon, cellulosic fibers, derivatives thereof, and blends therefrom. One skilled in the art will readily appreciate the effect of molecular weight, extent of crosslinking, presence of plasticizers and other additives, as well as other factors, that affect the fiber-forming abilities and fiber properties.

In one specific embodiment, the hydrophilic polymer is degummed silk. Silk is a fiber obtained from silkworms, more specifically from the larvae of mulberry silkworms. The silk most useful in the invention are those that can be woven into textiles, such as that obtained from the silkworm *Bombyx Mori*, however, other forms of silk that may be synthetically made or produced from other sources may also be used for this invention. Chemically, silk fiber comprises a chain of amino acids, which possesses functional groups that may be further used for binding useful moieties. As used herein, functional groups are reactive chemical moieties that can interact with other reactive species to form physical or chemical bonds.

The silk fiber obtained is then treated with an alkali solution to form at least one strand of degummed silk. The alkali solution useful in the invention is typically obtained by the dissolution of a compound having a strong basicity in an aqueous mixture. Typical compounds having strong basicity include, but not limited to, sodium hydroxide, potassium hydroxide, lithium hydroxide, calcium hydroxide, ammonium hydroxide and the like, and mixtures thereof. Treatment methods may include immersing the silk fiber into an alkali solution, spraying the silk-fiber with the alkali solution, or any such variation known to those skilled in the art. Without being bound to any theory or principle, it is known to one skilled in the art that silk fibers obtained in its natural state comprises a coating of a gummy mixture comprising a protein named sericin and that the alkaline solution can be used to efficiently remove the coating (Altman, G. H.; Diaz. F.; Jakuba, C.; Calabro, T.; Horan, R. L.; Chen, J.; Lu, H.; Richmond, J.; Kaplan, D. L., Silk-based biomaterials. *Biomaterials* 2003, 24 (3), 401-416). An optional washing step may be included to wash off the excess alkali or other extraneous material.

The hydrophilic polymer that may have been treated to render them suitable for further use is further immobilized with at least one of a first reagent, a second reagent or both, to form the diagnostic-fiber composition. In some instances, the first reagent is an antigen. Antigens useful in the invention include, for example p24, gp120, gp41, HIVII-gp105, gp36, Hepatitis C-NS3, NS5, core antigen, β-Hcg (pregnancy), TSH (thyroid), FSH (female hormone), Troponin-T (cardiac), CpkMb, BNP, Myoglobin, Hb1Ac, PSA, AFP, CEA, CA125, CA19.9, Progesterone, Testosterone, Estradiolin yet other instances, the first reagent is a primary antibody. Useful primary antibodies include, for example, Anti HBs (IgG), Anti HBc (IgM), Anti-hcG, Anti-HIV-p24, Anti-HIV-gp120, Anti-FSH, Anti-TSH, Anti Troponin, and Anti Plasmodium Falciparum, Toxoplasma IgM, Rubella IgM, Herpex Simplex Virus 2 IgM, Cytomegalovirus IgM, Typhidot IgM, Typhidot IgG, Dengue IgM, Dengue IgG, Leptospira IgM. In situations wherein a second reagent is present, the second reagent may be another primary antibody, or it may be a secondary antibody. In the case of a diagnostic-fiber composition having a primary antibody as the first reagent and a secondary antibody as the second reagent, it must be understood that the secondary antibody must be present upstream to the primary antibody taking into account the flow of fluids along the final diagnostic device. As used herein, the terms "upstream" and "downstream" are used to indicate the relative position with respect to the flow of a solution on the diagnostic-fiber composition. Thus, a spot on the diagnostic-fiber composition that comes into contact with a flowing solution first is considered upstream to a position on the diagnostic-fiber composition that comes into contact later.

Immobilization may be achieved by any number of techniques known to those skilled in the art. This may include, for example, immersing, covalent bonding, coating, dipping, stamping, or combinations thereof. Depending on the choice of the hydrophilic polymer, there may be included a step for the preparation of the polymer to receive the first and/or second reagent. For example, as already stated herein, silk may be degummed to facilitate the immobilization of the reagents, whereas a fiber made from poly(vinyl alcohol) may be amenable to immobilization with reagents as such.

In some embodiments, a further step of treatment with a suitable treatment solution may be necessary for the preparation of a diagnostic-fiber composition. The treatment solution may comprise a blocking agent to block any unused and exposed functional groups present on the hydrophilic polymer after the immobilization of the first and/or second reagent. Exemplary blocking agents include, for example bovine serum albumin, milk powder, and the like.

The treatment solution may further comprise a surfactant to enhance the flow of fluids by imparting better wicking abilities to the surface of the fiber. Suitable surfactants useful in the invention include, ionic surfactants such as perfluorooctanoate, perfluorooctanesulfonate, sodium dodecyl sulfate, ammonium lauryl sulfate, and other alkyl sulfate salts, sodium laureth sulfate, alkyl benzene sulfonate, cetyl trimethylammonium bromide, cetylpyridinium chloride, polyethoxylated tallow amine, benzalkonium chloride, benzethonium chloride, (3-[(3-cholamidopropyl)dimethylammonio]-1-propanesulfonate), dodecyl betaine, cocamidopropyl betaine, cocoampho glycinate; nonionic surfactants such as alkyl poly(ethylene oxide), poly(vinyl alcohol), sorbitan derivatives based on poly(ethylene glycol), including the Tween® series (ex. Tween® 20, Tween® 80), Span® series (ex. Span® 80) the Brij® series (ex. Brij® 72), the Triton® series (ex. Triton X-100), alkylphenol poly(ethylene oxide), copolymers of poly(ethylene oxide) and poly(propylene oxide) including the Pluronic® series (ex. Pluronic® F-127), alkyl polyglucosides, including: octyl glucoside, decyl maltoside, fatty alcohols such as cetyl alcohol, oleyl alcohol, dodecyl dimethylamine oxide; and the like. In one exemplary embodiment, the surfactant is a polysorbate based on poly (ethylene glycol), also sometimes referred to as sorbitan derivatives. In one specific exemplary embodiment, the surfactant is a Tween® 20. Further, a viscosity modifier such as a poly(ethylene glycol) may be applied to vary the flow rate to obtain the diagnostic-fiber composition.

The hydrophilic fiber may be treated with a treatment solution and then may be immobilized with at least one reagent. The order in which these actions are performed depend on the choice of the hydrophilic polymer, the nature of the intended device, the final application, and the like, and may be arrived at by one skilled in the art without undue experimentation.

An important criterion to pick a fibrous material suitable for making the diagnostic-fiber composition is its mechanical stability and the existence of manufacturing methods that are both precise enough to make intricate patterns and scalable such that large numbers of diagnostic-fiber compositions can be produced at a low cost. Silk is a material that fits both these criteria, and further, possesses other desirable properties such as being a natural fiber, biodegradable. Being a polypeptide, silk offers a number of functional groups that can be used to functionalize biomolecules. Further, silk weaving offers the ability to introduce particular functionalities into a pattern without resorting to high temperature or high shear processing. This involves simply treating the thread and incorporating it into a particular spot using weaving. Hence, in one embodiment, silk is the fiber used to make the diagnostic-fiber composition of the invention.

The method of making the diagnostic device of the invention further involves providing at least one strand of a hydrophobic-fiber composition, shown in FIG. 1 and represented by numeral 24. Hydrophobic as used herein refers to materials that are generally characterized by water-repellent property. Water repellence may be measured by techniques such as contact angle made by a drop of water on the surface of the material. Hydrophobic-fiber compositions are made from hydrophobic materials. Useful hydrophobic materials include polyamides such as, Nylon-66, Nylon-6, and other Nylons, Kevlar®; polyesters such as poly(ethylene terephthalate), poly(butylene terephthalate); poly(phenylene oxide); hydrophobic-coated silk, and the like, and combinations thereof. In one specific embodiment, the hydrophobic-fiber composition is a hydrophobic-coated silk. Typical hydrophobic coating useful in the invention include gold coating, tin coating, nickel coating, brass coating, copper coating, and the like.

The diagnostic device of the invention is made by the inter-weaving the at least one strand of the diagnostic-fiber composition and the at least one strand of the hydrophobic-fiber composition, represented by numeral 26 in FIG. 1. The method of inter-weaving is generally known among textile manufacturers. A useful method of inter-weaving includes the use of a double warp double weft technique. Other methods of introducing warp and weft are known in the art. Warp means the lengthwise yarns while weft means the yarn that is threaded through the warp. The angle between the warp and the weft can influence the flow properties within the diagnostic-fiber composition, and hence provides greater control over the use of the diagnostic device of the invention, which step is also included in the method of the invention. Currently, machines exist that are used extensively in the textile manufacturing industry for the production of finished textile goods using the double warp double weft technique along with other techniques.

A loom is an exemplary device used for weaving, and may be advantageously used for the production of the diagnostic device of the invention. Several types of looms are readily commercially available for use. Exemplary looms useful in the invention include, but not limited to, jacquard loom, dobby loom, treadle loom, power loom, and the like.

The method of the invention is particularly attractive as it is conducive for scale-up for manufacturing a large number of diagnostic devices within a given period of time. The method is also amenable to introducing multiplexed diagnostic devices. Currently, multiplexed devices known in the art that are capable of being used to detect more than one reagents, while they can be made in a lab-scale level, are generally faced with scalability in their manufacture. The method of the invention overcomes this drawback. The method of the invention further uses skill and equipment that already exist. In this invention, the adaptability of the existing methods in the textile manufacturing for the production of diagnostic device manufacture has been demonstrated successfully. The adaptation involves careful choice of materials and their preparation, and slight modification of the techniques to suit the requirements. Economic feasibility of the materials and methods also make this a viable option.

In yet another aspect, the invention provides a diagnostic device, as shown in FIG. 2 and represented by numeral 28. The diagnostic device comprises a diagnostic-fiber composition of the invention, represented in FIG. 2 by numeral 32 that is interwoven with a hydrophobic-fiber composition of the invention, that is represented by numeral 30 in FIG. 2. In one exemplary embodiment, a useful diagnostic-fiber composition of the invention comprises a degummed silk immobilized with at least a first reagent and treated with a treatment solution, as described herein. Useful hydrophobic-fiber composition of the invention comprises a gold-coated silk fiber. Interweaving methods are known in the field of textile manufacturing and may be made by the techniques described herein.

Figure 3:
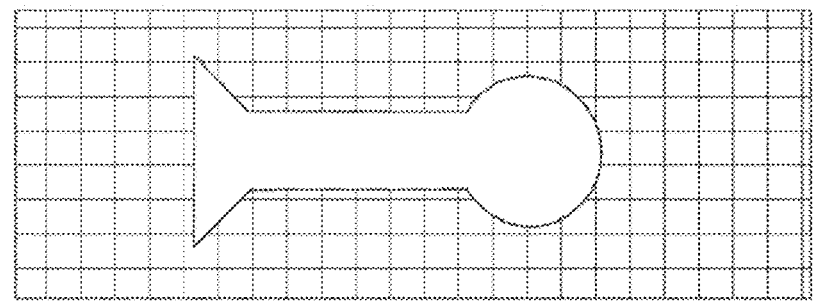
FIG. 3 shows schematic representations of another exemplary diagnostic device of the invention.
Figure 3:
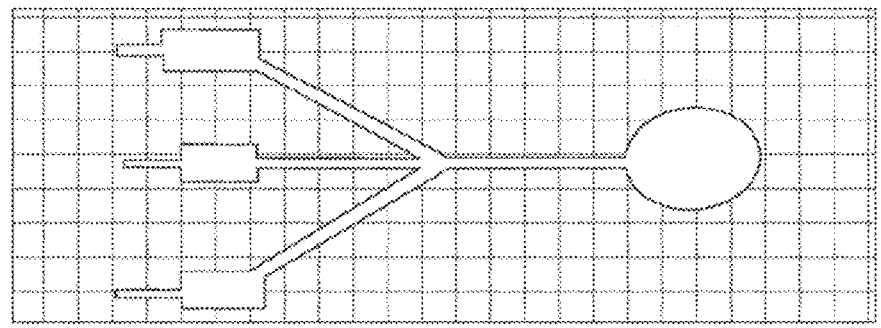

The shapes of the diagnostic-fiber composition in the diagnostic device of the invention may take any appropriate and useful shape necessary for the working of the invention. For simplicity sake, FIG. 2 depicts a rectangular shape for the diagnostic-fiber composition contained with a rectangular shaped hydrophobic-fiber composition. FIG. 3a shows another possible configuration for the diagnostic-fiber composition within the hydrophobic-fiber composition matrix. Similarly, FIG. 3b shows a possible configuration for the diagnostic-fiber composition for multiplexed analysis within a rectangular shaped hydrophobic-fiber composition. It will also be obvious to one skilled in the art that the hydrophobic-fiber composition may have any geometric shape.

Figure 4:
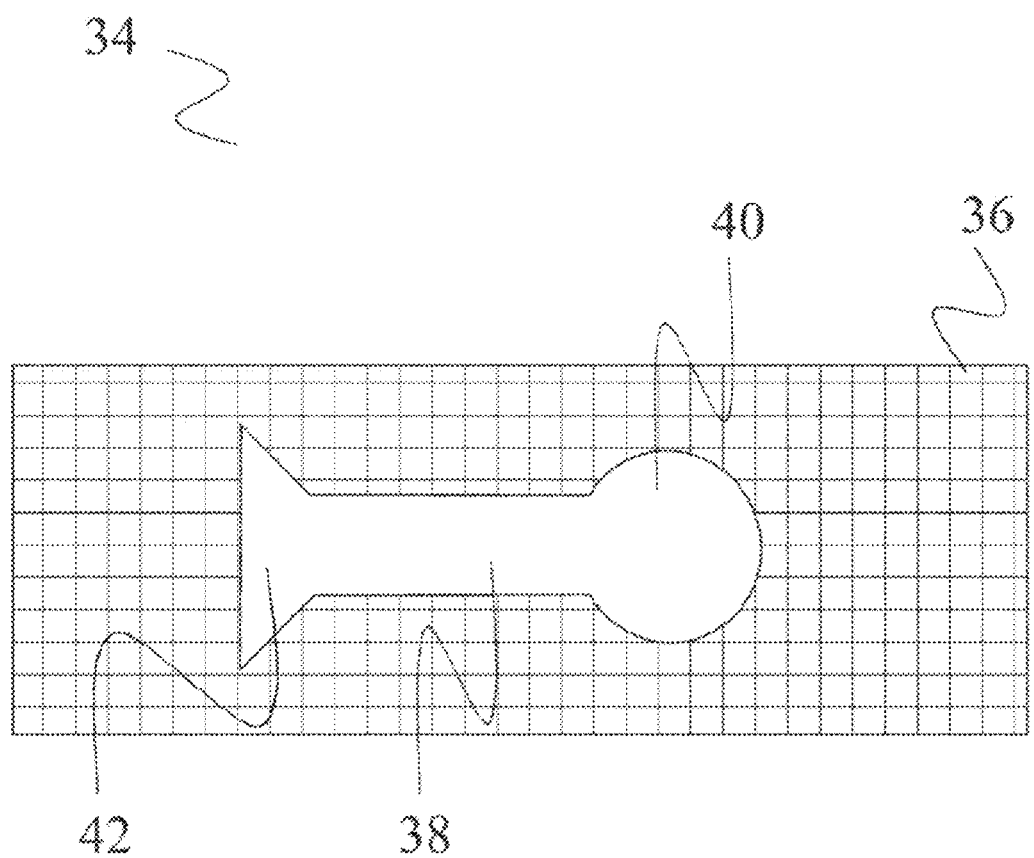
FIG. 4 shows a schematic representation of yet another exemplary diagnostic device of the invention.

The device of the invention can be used for diagnostic purposes. FIG. 4 shows one exemplary configuration of the diagnostic device of the invention. The diagnostic device is represented by numeral 34. The hydrophobic-fiber composition of the diagnostic device is represented by numeral 36. The diagnostic-fiber composition that is interwoven to the hydrophobic-fiber composition is represented by numeral 38. One end of the diagnostic-fiber composition is designated as a sample introduction port, and is shown in FIG. 4, represented by numeral 40. Typically, sample for analysis is introduced into the diagnostic-fiber composition as an aqueous solution or an aqueous suspension or an aqueous emulsion. The sample may comprise an analyte to be analyzed. Typical samples include, but not limited to, sweat, blood, urine, semen, and the like. Sample, as used herein, includes the entire fluid, or it may mean a component of the fluid that is being analyzed for. The nature of the analysis may be manifold. For example, in one embodiment, the analysis may involve determining presence or absence of an analyte. In another embodiment, the analysis may involve the concentration and/or amount of an analyte present in a sample. In some other embodiments, a combination thereof, which may include determining the presence or absence of an analyte, and if present, the amount and/or concentration of the analyte in the sample is to be determined. After introduction of the sample in the sample introduction port, the sample flows along the diagnostic-fiber composition. Without being bound to any theory, the solution will then flow through the diagnostic-fiber composition due to capillary action, also sometimes referred to as wicking action in the art. The device of the invention provides the advantage that the aqueous-based sample does not flow outside the diagnostic-fiber composition, thus reducing any sample losses, or other associated problems. The flow path culminates in an absorption port 42. In one embodiment, the reagent is present at a certain position on the diagnostic-fiber composition, and the absorption port is present in a flow direction that is past the position of the reagent on the diagnostic fiber composition such that the sample flows past the reagent and ends at the absorption port. In another embodiment, the reagent is added in a suitable manner known in the art, such that the reagent immobilization is achieved in situ. Subsequently, the sample is introduced onto the diagnostic-fiber composition. When the sample comprising the analyte and the reagent interact, they become bound and form a complex, and the complex stops flowing, while the solution flows till it reaches the absorption port 42. In case, the sample does not comprise the analyte, no complex is formed, and hence, the flow continues till it reaches the absorption port.

In situations wherein a secondary reagent is present, the sample comes in contact with the secondary reagent first as it is present upstream from the primary reagent and the analyte, if present, forms a first complex with the secondary reagent, following which the flow of the solution comprising the first complex reaches the primary reagent forming a second complex comprising the analyte, primary reagent and secondary reagent. The second complex stops flowing at this point. If the sample does not comprise the analyte, then the first complex and the second complex does not form, and the sample flows until it reaches the absorption port. The solution stops flow when there are no more flow regions remaining on the device. Flow regions would include the diagnostic-fiber composition which is hydrophilic in nature, and thus allows flow of the solution. Anything outside of the diagnostic-fiber composition, such as the hydrophobic-fiber composition would not be conducive for flow, and hence no flow will occur in that region. Further steps to remove unbound secondary reagent by washing it past the primary reagent by the excess sample fluid may also be contemplated. The analysis of the complex may be achieved through methods already known to those skilled in the art. Such methods may include, for example, fluorescence, confocal microscopy, optical microscopy, colorimetry, electrochemical methods, and the like, and combinations thereof.

In some embodiments, the sample port 40 may comprise a material that may facilitate addition of the sample and may further be useful in other additional functions, such as separating components. Some exemplary functions useful herein include separation of blood cells from fluids, separation of higher molecular weight components from low molecular materials, and the like. Specific compositions for achieving are known in the art, and may be suitably employed herein.

In some other embodiments, the absorption port 42 may further comprise an absorbent material, such as cotton, nitrocellulose, poly(acrylic acid), and the like to facilitate flow of sample.

Figure 5:
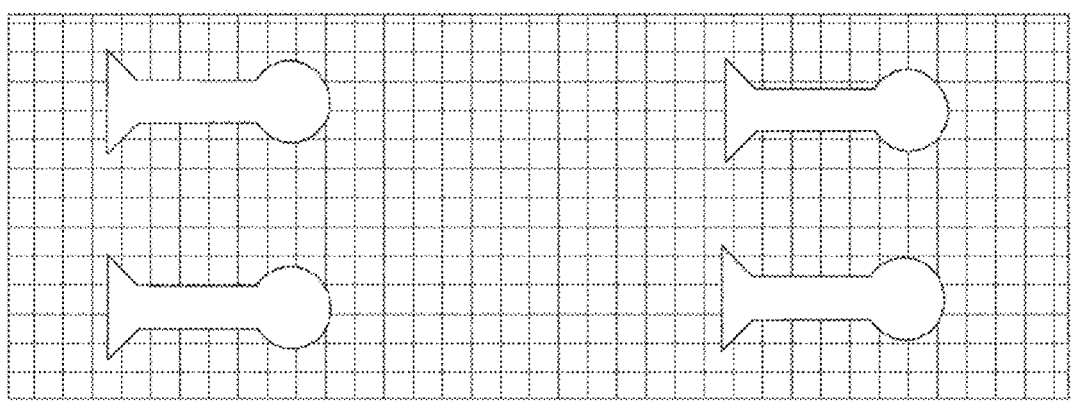
FIG. 5 shows a schematic representation of multiple diagnostic-fiber compositions in a hydrophobic-fiber composition, as another exemplary configuration of the diagnostic device of the invention.

It will also be obvious to one skilled in the art that a single hydrophobic-fiber composition may comprise more than one diagnostic-fiber composition, as shown in FIG. 5.

Figure 6:
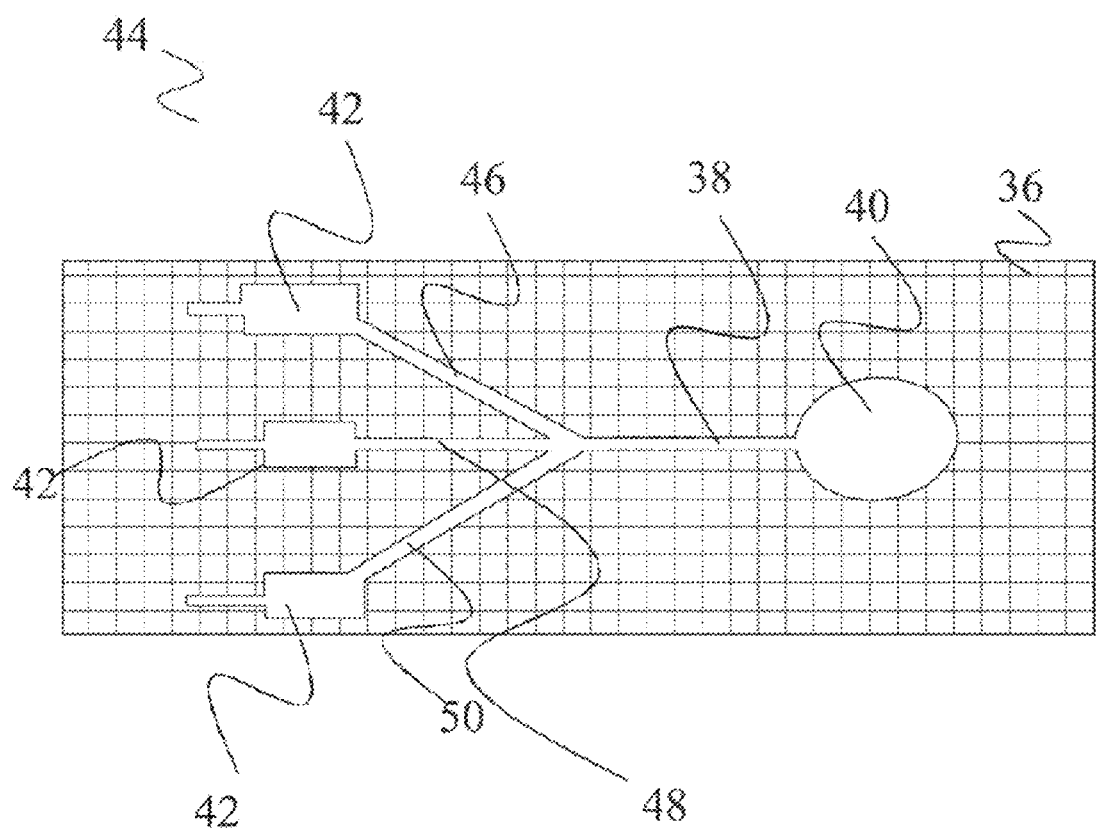
FIG. 6 shows an exemplary configuration of the diagnostic device of the invention that is used for multiplexed analysis.

FIG. 6 shows another exemplary diagnostic device used for multiplexed analysis as a further embodiment of the invention, wherein the device is represented by numeral 44. The device comprises the hydrophobic-fiber composition represented by numeral 36 and the diagnostic-fiber composition represented by numeral 38. The sample introduction port of the diagnostic device is represented by numeral 40, wherein the sample is introduced. The diagnostic-fiber composition has a shape wherein the flow of the sample is divided into three directions along three arms in this exemplary configuration, represented by numerals 46, 48 and 50. The arm represented by numeral 46 comprises a first reagent, while arm represented by numeral 48 comprises a second reagent and arm represented by numeral 50 comprises a third reagent. Thus, three different analyses are conducted simultaneously using this exemplary configuration for the diagnostic device of the invention.

Figure 7:
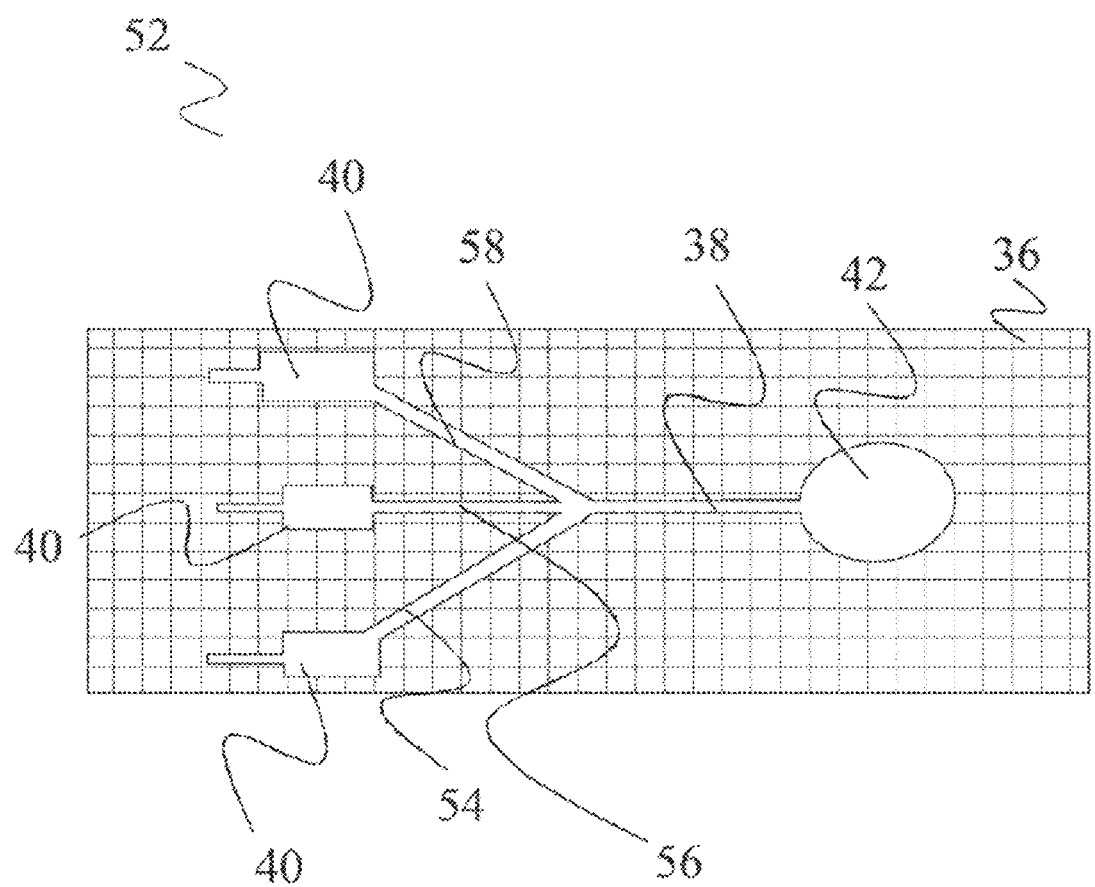
FIG. 7 shows yet another exemplary diagnostic device for analysis as a further embodiment of the invention.

FIG. 7 shows yet another exemplary diagnostic device for analysis as a further embodiment of the invention, wherein the device is represented by numeral 52. The device comprises the hydrophobic-fiber composition represented by numeral 36 and the diagnostic-fiber composition represented by numeral 38, wherein the diagnostic-fiber composition has the geometric configuration shown herein. The diagnostic-fiber composition comprises three different sample introduction ports 40, leading to three different flow paths corresponding to each sample introduction port, represented by numerals 54, 56 and 58 respectively. The three different flow paths in this exemplary configuration combine into one arm leading to the absorption port 42. This configuration of the diagnostic device is especially useful for immobilizing a first reagent in situ onto the diagnostic-fiber composition by allowing it to flow along the arm 54. Samples may be introduced simultaneously along arms 56. Thus, when the sample and the first reagent flows along arms 54 and 56, they meet at the body before reaching the absorption port 42. If the sample comprises an analyte of interest, it forms a complex with the first reagent and stops flow at the position. Further, a second reagent may also be added onto arm 56 at the same time as the first reagent and allowed to flow, while the sample is introduced onto arm 58 simultaneously. Thus, all three arms have three different components flowing simultaneously and meet at the body before reaching the absorption port 42. If the sample comprises an analyte of interest, it will interact with the first and second reagent to form a first and second complex, after which it stops flowing. Analysis of the complex may be performed using methods known in the art.

Figure 8:
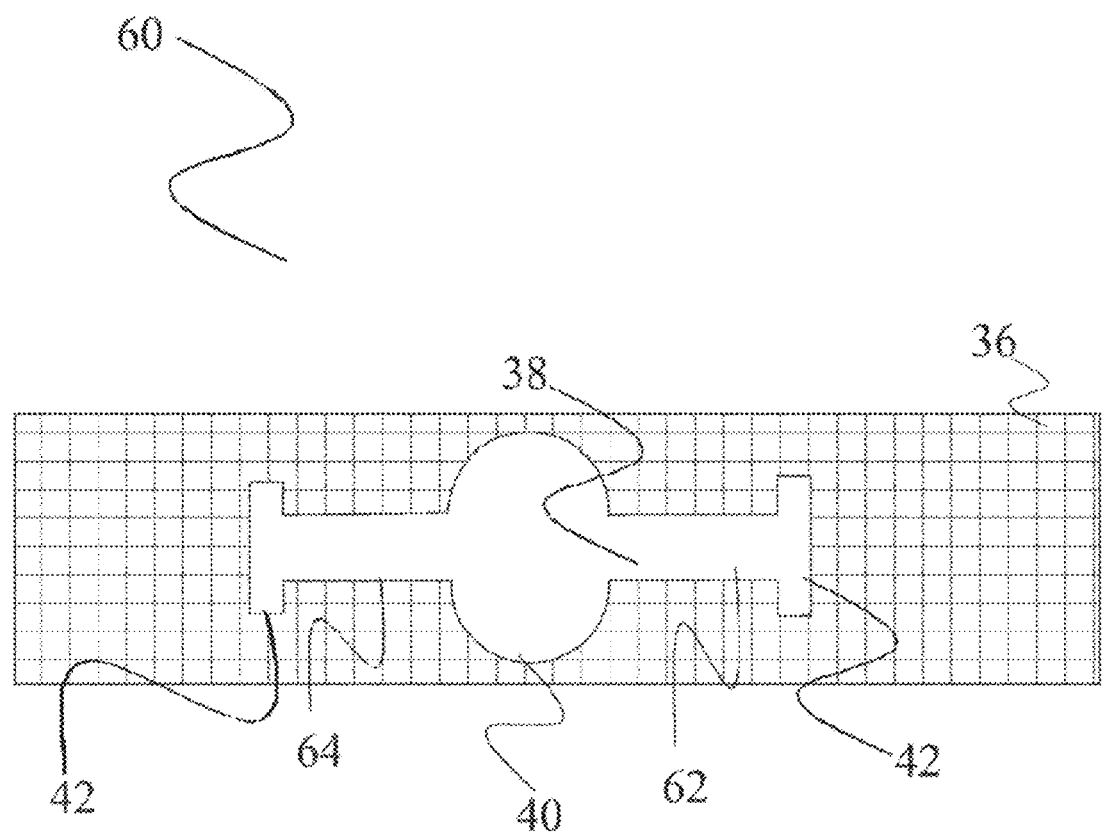
FIG. 8 shows yet another exemplary diagnostic device for analysis as a further embodiment of the invention.

FIG. 8 provides yet another exemplary diagnostic device for analysis as a further embodiment of the invention, wherein the device is represented by numeral 60. The device comprises the hydrophobic-fiber composition 36 and diagnostic-fiber composition 38, wherein the diagnostic-fiber composition has the geometric configuration shown herein. The sample introduction port 40 is situated in between two absorption ports 42. It will be obvious to one skilled in the art that the sample introduction port need not be necessarily in the center but the exact location will depend on the actual final configuration, function, manufacturing capabilities, and other such considerations. The sample once introduced into the sample introduction port will flow along all the directions wherever the diagnostic fiber composition extends, as determined by capillary flow. In the depicted exemplary configuration, sample flows along arms 62 and 64 until it reaches absorption ports 42 on either side of the sample introduction port, which may comprise two different reagents, or the same reagent, depending on the final function of the diagnostic device. In this manner, multiple analyses may be conducted on a single introduction of sample.

A typical diagnostic device may also comprise a marking to indicate the point to indicate the sample introduction port to a user. The amount of sample necessary to obtain a useful analysis from the diagnostic device of the invention will depend on the configuration of the device and may be arrived at without undue experimentation by one skilled in the art.

Figure 11:
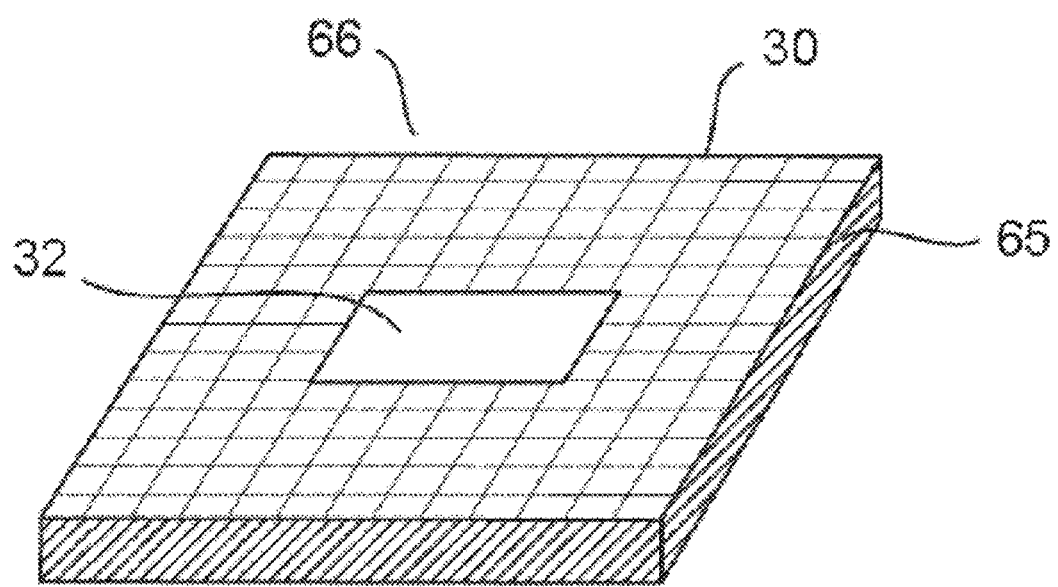
FIG. 11 is an exemplary diagnostic device of the invention, wherein the device comprises a solid substrate backing.

The diagnostic device of the invention may further comprise colorants, emollients, other additives for various purposes, along with those mentioned herein. These additives may be for cosmetic purposes, to provide extra features, or add greater functionality to the existing diagnostic device. Further, the diagnostic device of the invention may be mounted onto a substrate. The substrate may be present to provide strength and mechanical integrity to the device. The substrate may be chosen from any number of strong materials known to those skilled in the art, and may include, for example, metal backing such as steel, iron, titanium, alloys, and the like, plastics such as poly(methyl methacrylate), polystyrene, polyethylene, polypropylene, and the like, cardboard, wood, and others, and combinations thereof. A typical exemplary embodiment of the diagnostic device of the invention that has been mounted onto a substrate is shown in FIG. 11, wherein the substrate is represented by numeral 65.

The diagnostic device of the invention may further be contemplated to be encased in a suitable enclosure to protect it from environmental factors, such as handling during transportation, sunlight, moisture, humidity, and so on. In such instances, the enclosure may be designed in such a way that it can be opened to allow access to the device. Alternately, the enclosure may be present in such a way that there is an opening only for the sample introduction port, so that the rest of the device is totally enclosed even during operation. Enclosures suitable for the device may have properties such as transparency, strength, water resistance, moldability, and the like. Some useful materials that can perform well as enclosures for the device may include, but not limited to, glass, plastics such as poly(methyl methacrylate), polystyrene, polyethylene, polypropylene, and the like.

The invention as described herein provides weaving as an alternate manufacturing technology for the manufacture of fabric-based diagnostic devices that may also be referred to as 'fab chips'. Such diagnostic devices may be reusable type or may be a single-use, disposable device. Silk weaving is an art that has developed to a very high degree of skill in many parts of the world, and intricate patterns whose dimensions are limited only to the thickness of an individual thread may be woven in a highly parallelized manner. This technique is capable of being adapted for the manufacture of diagnostic devices of the invention in a facile manner. By weaving together both hydrophilic and hydrophobic fibers along with fibers that are coated with reagents, it is possible to manufacture a very large number of diagnostic devices, which are capable of single-plexing and multiplexing. Further, the reagents may be deposited onto very specific spots on the hydrophobic-fiber composition using known techniques in the art. This will result in the ability to actually fabricate an entire diagnostic device using only a loom. This provides a great advantage over the existing techniques which uses different manufacturing methods for various parts of the diagnostic device, thus complicating the process. Further, unlike the currently commercially available diagnostic devices, such as the paper-based devices which require different materials to function as the conjugation pad, absorption pad and sample delivery pad, the invention provides a single uniform manufacturing process to make the diagnostic device. Also, depending on the choice of the materials, a single base material, such as silk may be used to make the entire diagnostic device. This simplifies the manufacturing considerably. Also, when the diagnostic device of the invention is made using silk-based materials, it provides an added advantage in that silk is already used in sutures and in medical implants, which greatly enhances the diagnostic devices' chances of going through regulatory approvals.

The device of the invention may be used for any assays to be performed in a wide variety of applications. For example, in case of using the device of the invention for a sandwich immunoassay, sample for qualitative detection of antigen in the sample is introduced on to the sample port of diagnostic fiber composition of finished device. After introduction, as the sample flows along the diagnostic fiber composition due to capillary action, it comes in contact with secondary reagent (detection antibody) first, as it is present upstream from the primary reagent (capture antibody). Analyte (antigen) if present, forms a first complex with secondary reagent. Following this, the flow of the solution comprising the first complex reaches the primary reagent (capture antibody) forming a second complex comprising the analyte, primary reagent and secondary reagent. The second complex stops flowing at this point and can be visualized as pink/red color band. If the sample does not comprise the analyte, then the first complex and the second complex does not form, and the sample flows until it reaches the absorption port. The solution stops flow when there is no more flow regions remaining on the device.

In the case of the use of the device of the invention for an indirect immunoassay, the sample for the qualitative detection of antibody is introduced on to the sample port of diagnostic fiber composition of finished device. After introduction, as the sample flows along the diagnostic fiber composition due to capillary action, it comes in contact with secondary reagent (detection antibody) first, as it is present upstream from the primary reagent (capture antigen). Analyte (antibody) if present, forms a first complex with secondary reagent. Following this, the flow of the solution comprising the first complex reaches the primary reagent (capture antigen) forming a second complex comprising the analyte, primary reagent and secondary reagent. The second complex stops flowing at this point and can be visualized as pink/red color band. If the sample does not comprise the analyte, then the first complex and the second complex does not form, and the sample flows until it reaches the absorption port. The solution stops flow when there are no more flow regions remaining on the device.

Proof of Concept

For demonstration purposes, a degummed silk thread was wound around a plastic substrate made of poly(methyl methacrylate). This was then interwoven with a gold-coated silk thread such that the gold-coated silk flanked the degummed silk. Then, to this arrangement, an aqueous solution containing a green dye was spotted on one end of the degummed silk. Visually, it was determined that the aqueous solution containing the green dye did not spill into the hydrophobic regions and remained within the confines of the hydrophilic region of the device as evidenced by the lack of color in any region except along the hydrophilic degummed silk region.

Diagnostic Device

Figure 9:
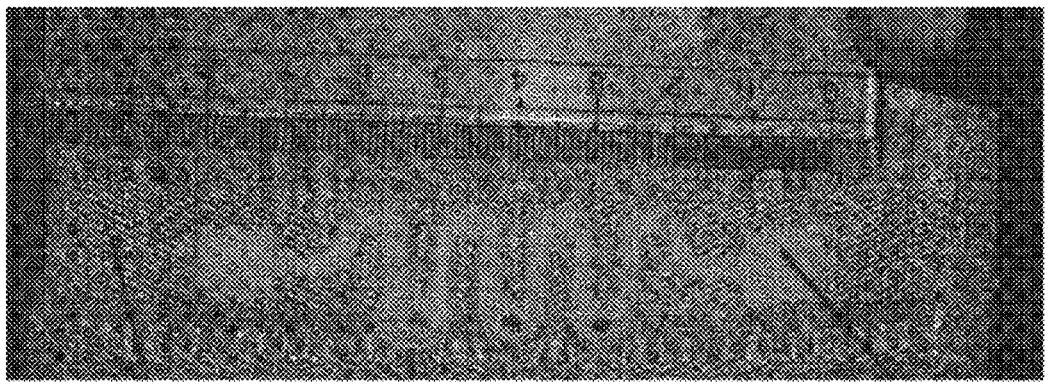
FIG. 9 is a photograph of the diagnostic device of the invention made by the method of the invention.
Figure 10:
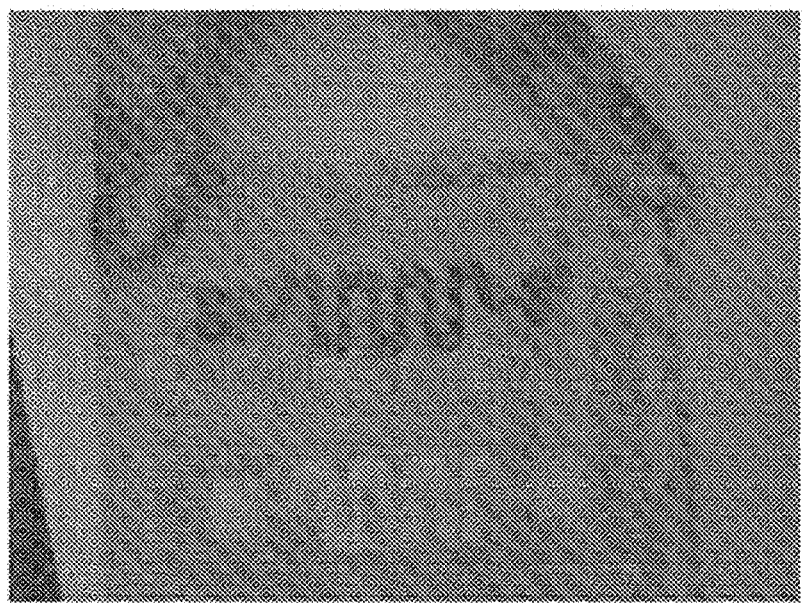
FIG. 10 is a photograph of the diagnostic device of the invention after it was wetted with an aqueous solution.

Based on the working proof-of-concept, a diagnostic device was designed and then woven. The design had three sinusoidal loops along the length of the diagnostic-fiber composition. The diagnostic device comprised white hydrophilic threads on a gold hydrophobic background. The diagnostic-fiber composition were colored with multiple colors for clearer visual identification for demonstration purposes, and were created by interweaving different colors at specific points in the pattern. These could function as capture antibody containing test lines. FIG. 9 shows the device as made by the method of the invention. The multiple colors on the diagnostic device can be visually identified by the three circular spots shown in FIG. 9. The diagnostic device was first tested for its wetting properties. A solution of green dye in water was loaded onto the sample delivery pad and flowed all the way to the absorption pad without leaking into the gold portion. FIG. 10 shows that the coloration is restricted to the degummed silk region, as shown by the darker coloration n the figure, while the hydrophobic gold-coated silk did not gain any color at all, as shown by the lighter coloration in the figure.

Example

Hydrophilic Fiber Composition

Natural silk fiber contains a waxy outer covering that must be removed by a process called degumming. Hydrophilic silk threads that permitted capillary flow were made by degumming the natural silk fiber by immersing the silk thread in a solution of 1M NaOH. The thread was then immersed in a solution containing 0.1% Tween® 20, Bovine Serum Albumin (BSA) and 1% PEG (MW 400). This treated thread was found to have more uniform flow properties and also prevented the non-specific binding of protein to the silk thread.

Hydrophobic Fiber Composition

While natural silk fiber can be used as the hydrophobic thread, we found that the natural fiber was not strongly hydrophobic enough to provide a contrast to the hydrophilic thread. On the other hand, readily available imitation "zari" thread which is golden in color made by coating silk with brass was found to be very hydrophobic in nature. Thus the brass-coated silk thread was used as the hydrophobic counterpart.

Capture Antibody/Antigen Coating on Threads

Since the degummed silk non-specifically binds to proteins, capture antibody was directly coated onto the hydrophilic fiber composition by immersing the hydrophilic fiber composition in an immunoglobulinG solution containing 1 mg/mL protein in Tris buffered saline.

Secondary Antibody Coating on Threads 40 nm sized Gold-conjugated secondary antibody was prepared using known methods (A. D. McFarland, C. L. Haynes, C. A. Mirkin, R. P. Van Duyne and H. A. Godwin, "Color My Nanoworld," *J. Chem. Educ.* 2004, 81, 544A; Secondary antibody conjugation to gold—Conjugation of Colloidal Gold to Proteins by Constance Oliver From: Methods in Molecular Biology, Vol. 115: Immunocytochemical Methods and Protocols Edited by: L. C. Javois© Humana Press Inc., Totowa, N.J.) The secondary antibody labeled gold solution, which was a clear, dark pink colored solution, was applied to the silk thread after first treating the silk thread with a solution containing 1% sucrose, 0.2% Tween 20, 1% Bovine Serum Albumin (BSA) and 1% poly(ethylene glycol) (Molecular Weight 400). The treated silk thread does not non-specifically bind to protein and the gold conjugate silk thread is only physically encapsulated in the interstitial spaces between silk threads allowing for it to leach out later.

Pattern formation: The first step in the formation of a fabric chip was forming a hydrophilic pattern on a hydrophobic background. Traditionally, three threads of pure Salem silk obtained from Kanchipuram, Tamil Nadu, India, are twisted together and woven using a double warp double weft technique. The Jacquard attachment in the loom enabled us to also achieve pattern versatility and intricacy. Patterned punched cards for the jacquard were generated using a computer program Cadvantage Win program made available by Teckmen Systems, India. The pattern was woven so that the fabric background surrounding the sinusoidal pattern was made from the hydrophobic, imitation gold thread. The entire exposed surface of the pattern itself was woven from hydrophilic, native, degummed silk thread which had been treated to improve the surface properties.

Coated Thread Incorporation

The capture antibodies and labeled secondary antibody coated thread was inserted at specified points between the hydrophilic warp threads manually, by a weaver, using individually labeled spools. Specific threads in the Jacquard controlled system are lifted and the coated thread is run through them using the shuttle. This results in coated thread being interwoven at multiple points in the fabric. A diagnostic device on which 3 tests could be conducted in sequence was made using this technique. At one end was a reservoir for loading the test sample. Downstream, one woven point was loaded with labeled secondary antibody, and three individual woven points were loaded with the appropriate capture antibodies. The device ended at an absorption pad. The finished device would permit the loaded test fluid to flow at a specified rate from the reservoir labeled secondary antibodies from the thread.

While only certain features of the invention have been illustrated and described herein, many modifications and changes will occur to those skilled in the art. It is, therefore, to be understood that the appended claims are intended to cover all such modifications and changes as fall within the true spirit of the invention.

We claim:

1. A method of making a diagnostic device, said method comprising:
    providing at least one strand of a diagnostic-fiber composition, wherein the diagnostic-fiber composition comprises degummed silk immobilized with at least one of a first reagent, a second reagent or both;
    providing at least one strand of a hydrophobic-fiber composition;
    inter-weaving the at least one strand of the diagnostic-fiber composition and the at least one strand of the hydrophobic-fiber composition, wherein the inter-weaving between the strands is configured to result in an angle between the strands which provides greater control to affect flow properties of the at least one strand of the diagnostic-fiber composition wherein the strand of the diagnostic-fiber composition and the strand of the hydrophobic-fiber composition are wound relative to one another.

2. The method of claim 1, wherein the hydrophobic-fiber composition is derived from the group consisting of polyamides, polyesters, hydrophobic-coated silk, and combinations thereof.

3. The method of claim 2, wherein the hydrophobic-fiber composition is hydrophobic-coated silk.

4. The method of claim 1, wherein the inter-weaving is achieved using a double warp double weft technique.

5. The method of claim 4, wherein the inter-weaving is achieved using a loom.

6. The method of claim 5, wherein the loom is a jacquard loom.

7. The method of claim 5, wherein the loom is a dobby loom.

8. The method of claim 5, wherein the loom is a treadle loom.

9. The method of claim 5, wherein the loom is a power loom.

10. A diagnostic device made by a method comprising:
    providing at least one strand of a diagnostic-fiber composition, wherein the diagnostic-fiber composition comprises degummed silk immobilized with at least one of a first reagent, a second reagent or both,
    providing at least one strand of a hydrophobic-fiber composition, and
    inter-weaving the at least one strand of the diagnostic-fiber composition and the at least one strand of the hydrophobic-fiber composition, wherein the inter-weaving between the strands is configured to result in an angle between the strands which provides greater control to affect flow properties of the at least one strand of the diagnostic-fiber composition wherein the strand of the diagnostic-fiber composition and the strand of the hydrophobic-fiber composition are wound relative to one another.

11. A diagnostic device comprising:
    at least one strand of a diagnostic-fiber composition, wherein the diagnostic-fiber composition comprises degummed silk immobilized with at least one of a first reagent, a second reagent or both; and
    at least one strand of a hydrophobic-fiber composition that is inter-woven with the at least one strand of diagnostic-fiber composition, wherein inter-weaving between the strands is configured to result in an angle between the strands which provides greater control to affect flow properties of the at least one strand of the diagnostic-fiber composition wherein the strand of the diagnostic-fiber composition and the strand of the hydrophobic-fiber composition are wound relative to one another.

12. The diagnostic device of claim 11, wherein the hydrophobic-fiber composition is hydrophobic-coated silk.

13. The diagnostic device of claim 11, wherein an interweave pattern of warp and weft of the at least one strand of a diagnostic-fiber composition and at least one strand of a hydrophobic-fiber composition is made by using a double warp double weft technique.

14. The diagnostic device of claim 13, wherein the interweave pattern of warp and weft is made by using a loom.

* * * * *